US00PP36298P2

(12) United States Plant Patent
Young-Bustillo et al.

(10) Patent No.: US PP36,298 P2
(45) Date of Patent: Dec. 10, 2024

(54) PINEAPPLE PLANT NAMED 'HND-32'

(50) Latin Name: *Ananas comosus*
Varietal Denomination: HND-32

(71) Applicant: Dole Food Company, Inc., Charlotte, NC (US)

(72) Inventors: Roberto Antonio Young-Bustillo, La Ceiba (HN); Fernando Alberto Molina-Salinas, La Ceiba (HN); Douglas Neptalí Cárdenas-Cárdenas, La Ceiba (HN)

(73) Assignee: Dole Food Company, Inc., Charlotte, NC (US)

( * ) Notice: Subject to any disclaimer, the term of this patent is extended or adjusted under 35 U.S.C. 154(b) by 0 days.

(21) Appl. No.: 18/510,078

(22) Filed: Nov. 15, 2023

(51) Int. Cl.
*A01H 5/08* (2018.01)
*A01H 6/22* (2018.01)

(52) U.S. Cl.
USPC ..... Plt./156

(58) Field of Classification Search
USPC ..... Plt./156
CPC ... A01H 5/08; A01H 5/00; A01H 5/02; A01H 6/22
See application file for complete search history.

(56) References Cited

PUBLICATIONS

International Code of Nomenclature for Cultivated Plants, Ninth Edition, published by ISHS 2016, 2 cover pages and pp. 49-50. (Year: 2016).*
Trademark Electronic Search System retrieved on Mar. 18, 2024 at https://tsdr.uspto.gov/#caseNumber=75457932&caseSearchType=US_APPLICATION&caseType=DEFAULT&searchType=statusSearch, 2 pp. (Year: 2024).*
UPOV International Union for the Protection of New Varieties of Plants UPOV/EXN/DEN/3 2023, retrieved on Mar. 18, 2024 at https://www.upov.int/edocs/expndocs/en/upov_exn_den.pdf, pp. 1 and 10-11. (Year: 2023).*

* cited by examiner

*Primary Examiner* — June Hwu
(74) *Attorney, Agent, or Firm* — Klarquist Sparkman, LLP

(57) ABSTRACT

A new pineapple (*Ananas comosus*) variety of the Bromeliaceae family was developed from a cross between the parental genotype 'Dole-12' and the commercial variety 'Dole-11' and has been designated 'HND-32'. This new variety combines from its progenitors' different characteristics producing a unique hybrid showing irregular presence of spines in leaf margins, green leaves with red mottling colors, a reddish inflorescence at bottom stage, a cylindrical-slight taper shaped fruit with a long-conical crown, a distinctive ochre shell color, and an ivory white pulp with balanced sweet/acid-pleasant flavor, and tolerance to natural flowering differentiation.

5 Drawing Sheets

Specification includes a Sequence Listing.

Latin name of the genus and species of the plant claimed: *Ananas comosus*.

Variety denomination: 'HND-32'.

INCORPORATION OF SEQUENCE LISTING

The electronic sequence listing, submitted herewith as a XML file named "Sequence" (7,651 bytes), created on Sep. 19, 2023, is herein incorporated by reference in its entirety.

BACKGROUND OF THE INVENTION

Pineapple is a popular fruit worldwide. There is a continued need for improved varieties, particularly those varieties with distinct pulp color combined with novel and enjoyable fruit flavor.

BRIEF SUMMARY OF THE INVENTION

The invention refers to a new plant variety of pineapple (*Ananas comosus*) family Bromeliaceae, subclass of Monocotyledons, and named 'HND-32'. The fruit has a distinct ochre shell color with a whitish pulp, and a unique and pleasant combination of sweet-acid flavor. The fruit shape is cylindrical, tapering slightly from near the base, and with a long conical crown. This new variety is tolerant to natural flowering differentiation (NDF).

The new pineapple (*Ananas comosus*) variety, 'HND-32', inherited several traits from its female parent including compact plant architecture with green leaves showing anthocyanin pigments, reddish inflorescence at bottom stage, the ochre color of the shell with whitish pulp, and tolerance to NDF; and from its male side received spiny leaves and a long conical crown. 'HND-32' shows a consistent ochre shell color when ripen, and a persistent enjoyable sweet-acid flavor compared to its progenitors.

BRIEF DESCRIPTION OF THE DRAWINGS

The accompanying photographs depict the new variety 'HND-32' and its progenitors: 'Dole-12' and 'Dole-11'.

DETAILED DESCRIPTION OF THE INVENTION

Figure 1A:
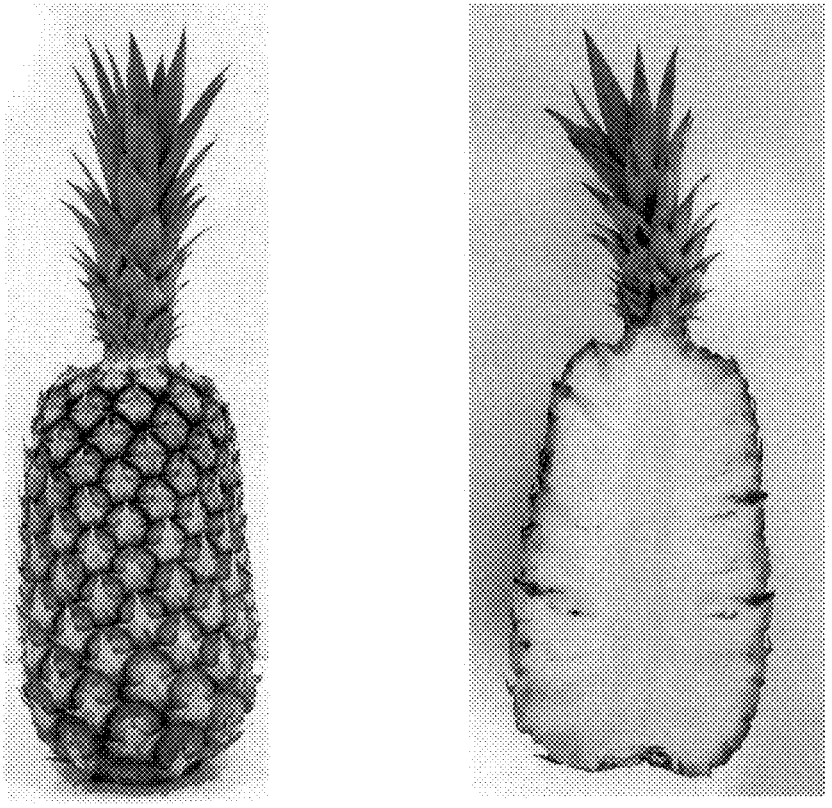
FIG. 1A shows fruit shell (left) and pulp (right) of the female parent 'Dole-12'.
Figure 1B:
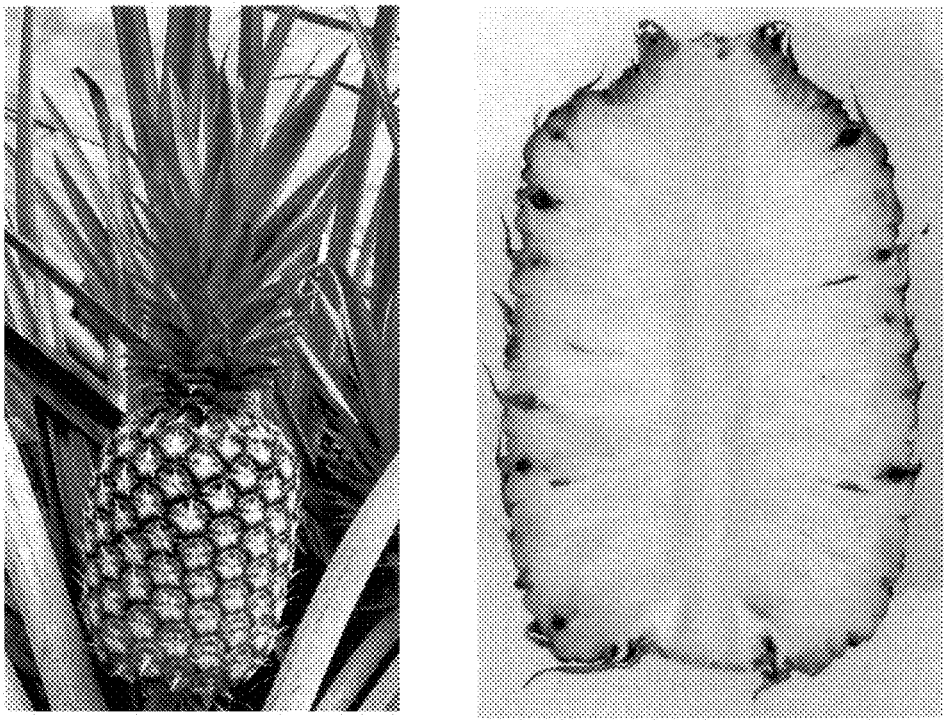
FIG. 1B shows fruit shell (left) and pulp (right) of hybrid 'HND-32'.
Figure 1C:
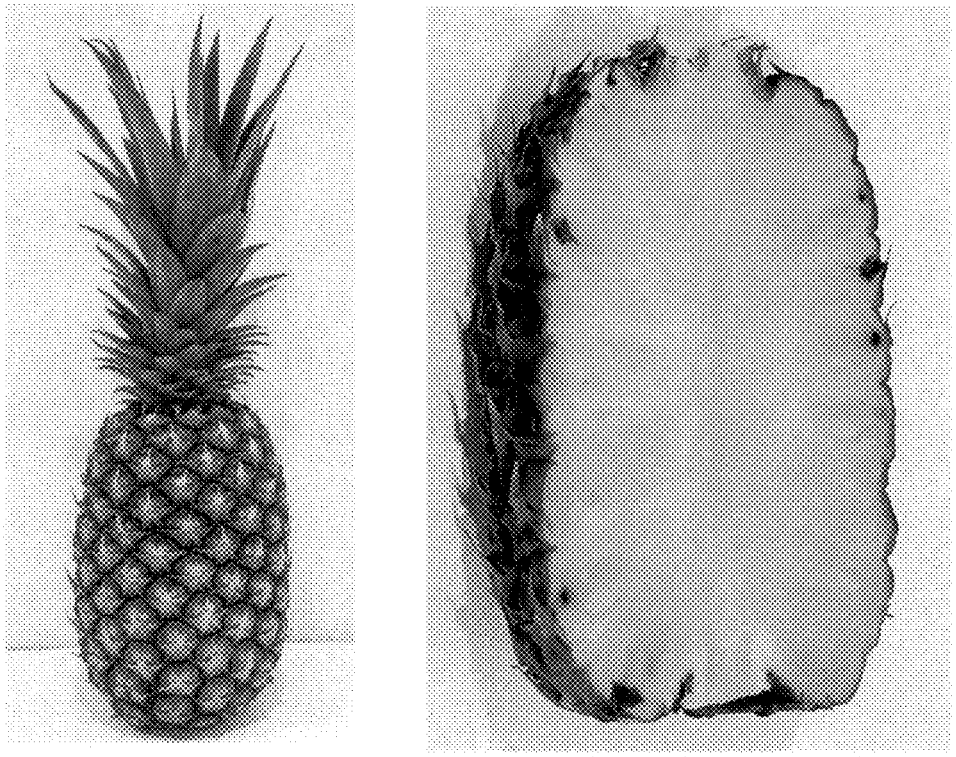
FIG. 1C shows fruit shell (left) and pulp (right) of the male parent 'Dole-11'.
Figure 2A:
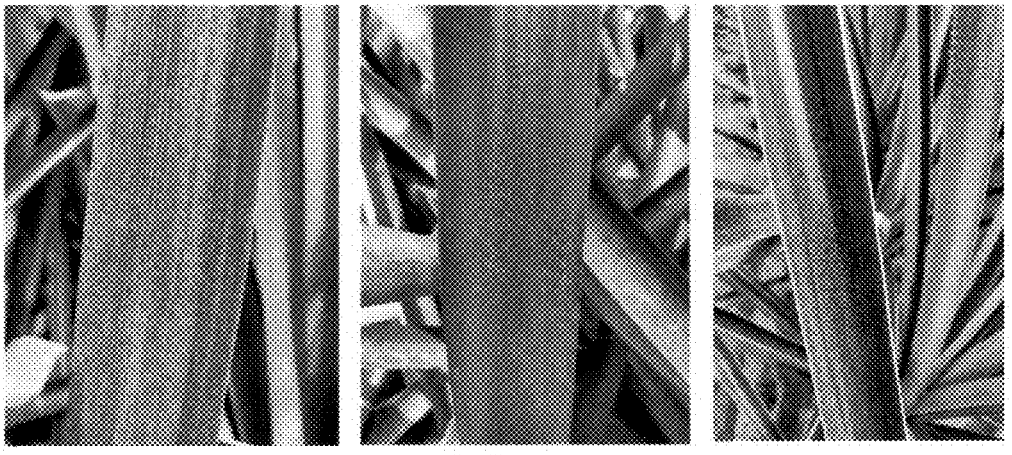
FIG. 2A shows the green leaf color with anthocyanin of 'HND-32' (left), the light green color of 'Dole-11' (middle), and green color with anthocyanin of 'Dole-12' (right).
Figure 2B:
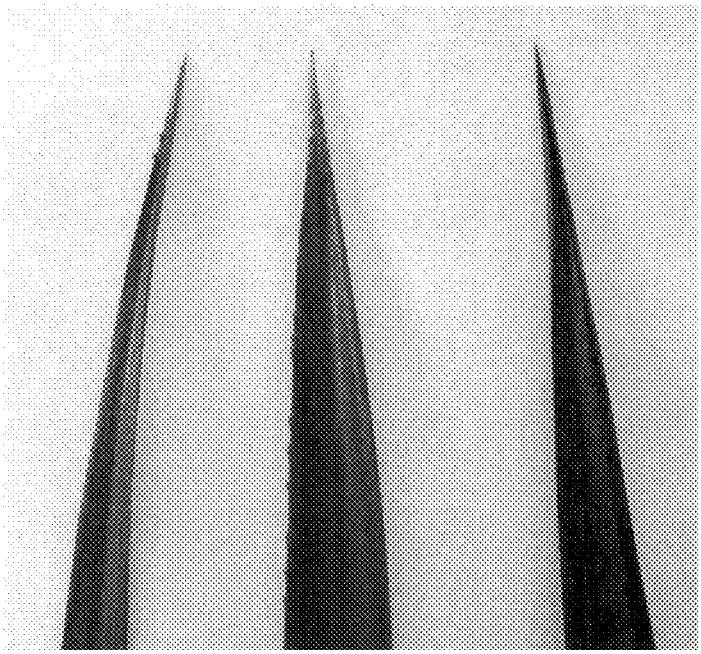
FIG. 2B shows young leaf tip with spines of 'HND-32' (left), the spiny tip of 'Dole-11' (middle), and the spineless tip of 'Dole-12'(right).
Figure 2C:
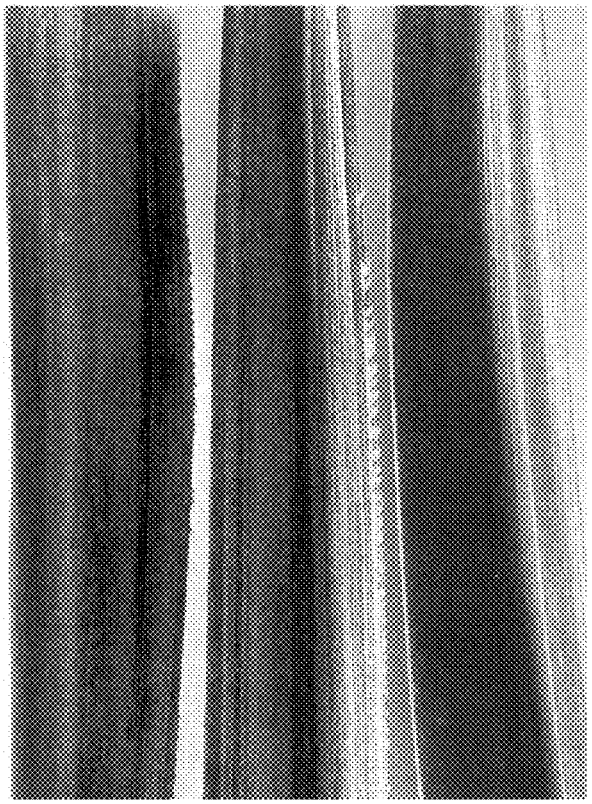
FIG. 2C shows adult leaf margin with spines of 'HND-32' (left), spiny leaf margins of 'Dole-11' (middle), and leaf margin with piping of 'Dole-12'. (right).
Figure 2D:
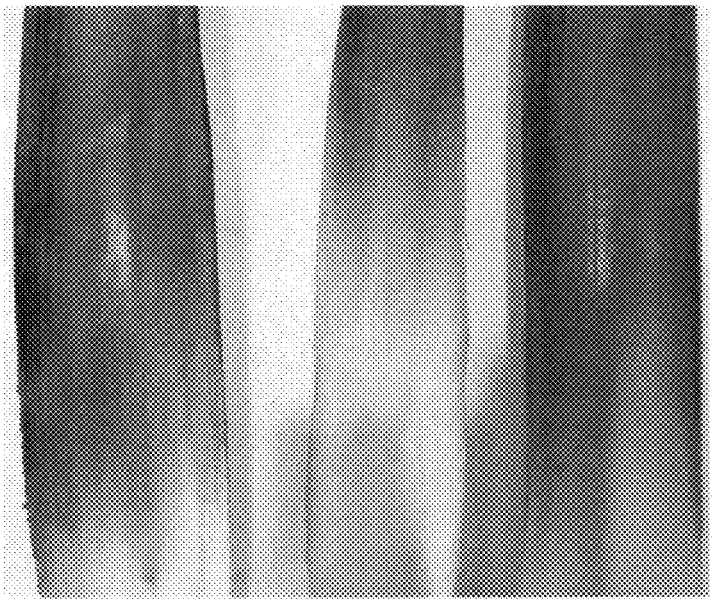
FIG. 2D shows brownish basal leaf color with spines of 'HND-32' (left), light green-yellowish and spiny basal leaf of 'Dole-11' (middle), and brownish basal leaf with piping of 'Dole-12'. (right).
Figure 3:
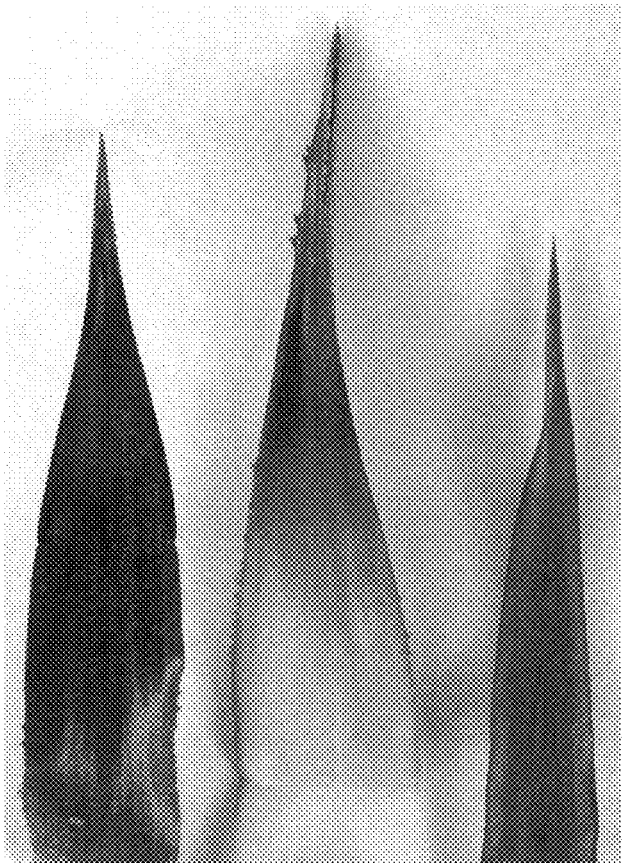
FIG. 3 shows peduncle bracts of 'HND-32' (left), 'Dole-11' (middle), and 'Dole-12' (right).
Figure 4:
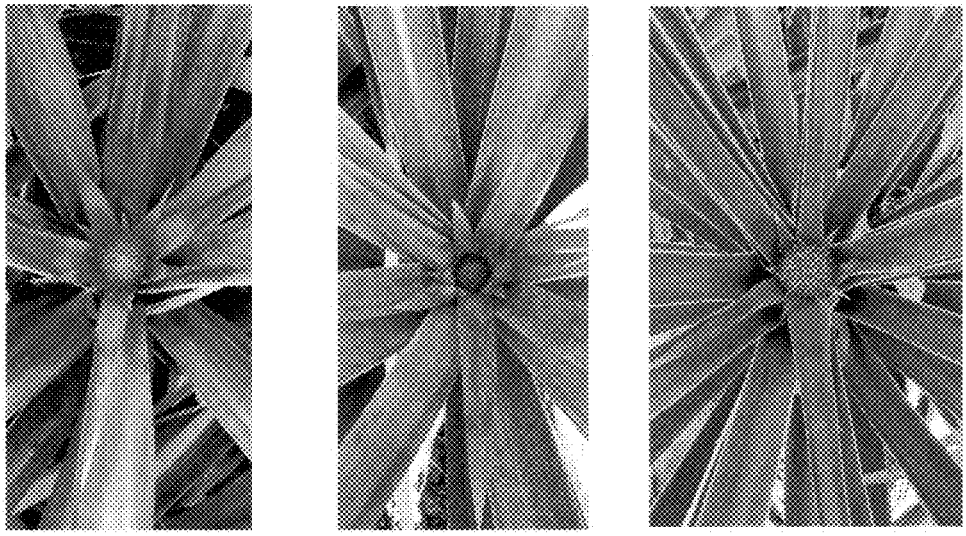
FIG. 4 shows reproductive bottom stage of 'HND-32' (left), 'Dole-11' (middle), and 'Dole-12' (right).

'HND-32' was originally selected during May 2012 as an individual plant within a segregating population produced from seed from a cross carried out in 2009 between 'Dole-12' (unpatented) and 'Dole-11' (unpatented) and named '0912MC-12/11-155'. Testing and selection of three consecutive asexual generations took place from May 2012 through October 2016, in Honduras, Central America.

Parental Description: 'Dole-12' used as the female parent was originally obtained from a research center in Hilo, Hawaii, and identified as 'Hana 57'. 'Dole-12' possess a distinctive ochre shell color which could develop into an orange like color during the cold/rainy season. The plant shows an erect plant habit, upright foliage attitude, long spineless leaves with piping of whitish in color, and green leaves with reddish tones due to the presence of anthocyanin pigments. The inflorescence at bottom stage shows a unique red color. The plant bears a uniform cylindrical-slight taper and with a smooth and thin shell and flat fruitlets or eyes, and it develops few slips by harvest time. Fruit is borne on a long peduncle and the crown is lengthened cylindrical with a weight around 100 g. 'Dole-12' has unique characteristics such as distinctive fruit aroma, high Brix with a tendency to a sweet/acid flavor, and ivory white flesh color. Incidence of FCR (Fruitlet Core Rot, caused by *Fusarium moniliforme*) and IB (Internal Browning) is high in 'Dole-12', but it shows tolerance to natural flowering differentiation (NDF).

'Dole-11' used as the male parent, was derived from crossing Pineapple Research Institute of Hawaii hybrid clones 58-1184 and 59-443. 'Dole-11', also known as Tropical Gold® pineapple, is a popular commercial variety appreciated for its yellow and golden yellow shell and pulp color when ripen respectively. Regularly, leaf margins in 'Dole-11' are devoid of spines: however, spines may be present, and their abundance and distribution may vary depending on the environmental conditions. The inflorescence at bottom stage shows a unique green-yellow color. Fruit is mostly conical to cylindrical-sharp taper in shape, with a long conical and attractive crown, and weighing approximately 1.9 Kg. The flesh in 'Dole-11' is smooth in texture, with small to intermediate amount of fiber, and with high content of vitamin C. 'Dole-11' develops a yellow color pulp, with a Brix/Acid ratio ranging from 28°-35°, favoring a pleasant and mostly sweet flavor. 'Dole-11' is resistant to both FCR (Fruitlet Core Rot) caused by *Fusarium moniliforme*, and Blackheart, but it is highly susceptible to Root Rot caused by *Phytophtora cinnamomi*.

This breeding effort aimed to produce a fresh fruit variety with high yield potential, tolerance to natural flowering, distinctive pulp color, and with unique and enjoyable pulp flavor. The development of the new variety started during 2009 in the North coast of Honduras (USDA Hardiness Zone: approximately 13 B, temperature >65° F./18.3° C.). A segregating population was produced by cross-pollinating flowers of 'Dole-12' with pollen taken from plants of the variety 'Dole-11'. The first plant selection was practiced in year 2012 and was identified as '1215MC-12/11-155' later named 'HND-32'. Different methods of asexual propagation were used for variety multiplication, i.e., stem cuttings, slips, suckers, gouging of fruit crowns, and tissue culture derived plants. Genetic stability of the selected hybrid was evaluated during three consecutive asexual generations, using plantlets derived from gouged crowns as planting material, from 2012 through 2016 at Montecristo farm in El Porvenir, Atlántida. 'HND-32' shows unique characteristics such as irregular presence of spines in leaf margins, green leaves with red mottling colors, a cylindrical-slight taper shaped fruit with a crown that is long-conical, a reddish inflorescence at bottom stage, a distinctive ochre color of the shell, and a balanced sweet/acid pulp flavor particularly during the dry warm season. Conducive NDF conditions (temperature < 64.4° F./18.0° C., cloudiness, photoperiod of 11 hours, high soil saturation) occurring in the North Coast of Honduras during three consecutive winter seasons (November-March) revealed that the new pineapple hybrid 'HND-32' is tolerant to natural flowering. The new variety is stable and has reproduced true to type in three successive generations of asexual reproduction. The new variety was developed for the fresh fruit market. In shipping simulations (45° F./7.2° C.), the fruit kept its freshness for up to three weeks.

DETAILED BOTANICAL DESCRIPTION OF THE PLANT

The following is a description of the new plant variety based on observations made prior to forcing and after forcing during May of 2022 and January of 2023, and at harvesting in October through November of 2022 and July of 2023; grown in the North Coast of Honduras (15 degrees 44 minutes latitude north, and 86 degrees 53 minutes longitude west). The average temperature in the North Coast Honduras is 26° C.; with 3,542-mm of annual average precipitation. The Munsell Color Chart was used for all color designations (Munsell Book of Color Gretag Macneth LLC, 617 Little Britain Road, New Windsor, New York 12553-6148).

Name: *Ananas comosus* (L.) Merr. Var. 'HND-32', family Bromeliaceae, subclass Monocotyledons.

Parentage: I. Seedparent. Variety 'Dole-12'. II. Pollen parent. Commercial variety 'Dole-11'.

Classification: I. Botanic.—Family: Bromeliaceae. Subfamily: Bromeliacidae. Genus: *Ananas*. Species: *Comosus*. Cultivars: 'Dole-12' x 'Dole-11'. II. Commercial.—Bromeliad fruit plant.

*General form*.—During the vegetative stage the plant growth habit of 'HND-32' is upright, showing a normal posture with an upright foliage attitude and consists of a compact rosette of overlapping sessile leaves arising from a central stem and surrounding a composite inflorescence prior anthesis. Production of offshoots (suckers, hapas and slips) is usually absent, but depending on season hapas may vary from 1 to 3 per plant. Plant height at forcing time was on average 148.2 ± 4.1 cm, but it may vary depending on growing conditions. Plant diameter was 5.7 ± 0.4 cm, measured at the base and at forcing time in a 3.2 ± 0.1 Kg plant.

*Stems*.—Stem is upright, sheathed by overlapping leaves arranged in acropetal fashion, forming a heart shape stem. The stem color is greyish (5Y 8/2, 8/4, 7/2). Stem length was 46.6 ± 4.7 cm, measured from the plant's base to the peduncle's base.

Leaves: I. General.—leaves are sessile, trough shaped, tapered from base to tip, elongated and succulent, with acuminate apex, and forming a rosette with a 5/13 phyllotaxy. Depending on growing conditions, the average number of leaves per plant is 62.8 ± 0.6. The breakage resistance of the leaf is medium, and foliage attitude is upright (Descriptors for Pineapple, IBPGR, Rome 1991). Trichomes are present in the abaxial side of the leaves. II. Color:—The color of the upper surface of the D leaf is dark green (7.5 GY 3/4, 4/4) with red mottling (5 R 3/4, 3/6) and in the lower surface is pale pink (2.5 R 7/6, and 5 R 7/6). The intensity of the anthocyanin pigment in the leaves may vary from medium to very strong depending on the time of the year. III. Margins. The leaves show irregular presence of spines along the margins, mainly on tip and base, depending on the season. Unlike its female parent, Dole-12, it shows no piping. The margin color is dark brown darker (10 R 3/2). The longest leaf thickness is on average 1.4 ± 0.2 mm at middle section. IV. Leaf size.—Average length on D leaf is 136 ± 6.0 cm, and average width is 6.6 ± 0.6 cm at middle section.

Inflorescence: I. General.—Pineapple inflorescence of composite flower, with self-incompatible individual bi-sexual flowers containing three sepals (11.2 ± 0.7 mm in length), three petals (23.9 ± 0.8 mm in length, 5.6 ± 0.5 mm wide), six syngenesious stamens (19.0 ± 0.8 mm in length and cream in color), the yellowish (5 Y 8/6) anthers are heart-shaped with a dorsifixed attachment (2.96 ± 0.2 mm in length) and bearing abundant pollen. The gynoecium is composed of an axile ovary (three carpels 6 to 7 mm in length) of cream color and a whitish style (length 23.2 ± 0.7 mm) with a lobed-shaped stigma. The inflorescence is borne in a long conical and slender peduncle (35.0 ± 1.6 cm in length, and 1.9 ± 0.1 cm in diameter at middle section). The number of days to flowering after forcing is as follows: 39 days to the presence of a distinctive reddish floral bud, and 58 days to mid flower. The inflorescence height at mid flower stage is 11.5 ± 0.4 cm. The inflorescence diameter at mid flower stage is 6.5 ± 0.1 cm. II. The peduncle bract has a lanceolate form, with an acute apex, acuminate base, and margins with few spines. Bract color in the adaxial side is green at the tip (7.5 GY 3/4), red mottling in the middle section (2.5 R 5/8, 4/8), and pink at the base (2.5 R 6/8, 6/10). The bract color in the abaxial side is green (5 GY 5/8, 6/8) at top and reddish at the base (5 R 4/10, 5/10, 6/10). The average number of peduncle bracts is 22.7 ± 1.1, with the longest bract length of 69.8 ± 4.1 cm, and width of 5.0 ± 0.6 cm, and the shortest bract length of 3.3 ± 0.1 cm, and width of 2.7 ± 0.2 cm. The floral bract, which covers 2/3 of the flower, is of aristate apex and truncate base. The floral bract is 23.1 ± 0.7 mm in length, 13.0 ± 0.8 mm wide and has a smooth edge. The floral bract color at the adaxial side of the tip is reddish (5 R 4/10, 5/10, 6/10), and greenish at the base (5 GY 7/10, 6/10, 5/10). The floral bract at the abaxial side is light green (7.5 GY 8/4, and 5 GY 5/8, 6/8). III.—Petals have entire margins with an oblong shape and a closed orientation. The apex is subacute, and the base is truncate. Petal color is white at the base, pink in the middle section (5 RP 8/6, 7/6) and deep purple at the tip in both surfaces (5 RP 4/12, 3/8). IV. The sepals have entire margins with an orbicular shape and obtuse apex. In the adaxial side the coloration of the tip is dark brown (5 R 3/4, 3/6), the middle section is green (5 GY 5/10) and light green at the base (5 GY 7/10, 6/10). In the abaxial side is brownish to orange in the tip (10 R 5/6), and light green at the base (5 GY 7/4, 7/8), with trichomes.

Fruit: I. Fruit shape. The fruit shape is cylindrical, tapering slightly from near base with 19.7 ± 3.0 cm in height, and with a diameter of 13.4 ± 0.5 cm at middle part, and the shell is smooth with 8-9 mm thickness. The number of fruitlets is 145.3 ± 1.8, averaging 9.0 ± 0.1 spirals per fruit, and 16.3 ± 0.4 fruitlets in the longest spiral. The coloration of the fruitlet is ochre (7.5 YR 7/10, 6/10) and it has a mammiform shape apex. The fruitlet height is 19.7 ± 1.5 mm and 16.8 ± 1.3 mm width. II. Fruit and crown average heights are 19.7 ± 3.0 cm and 23.7 ± 3.6 cm respectively for a fruit/crown ratio of 0.85. Mean fruit weight with crown is 2.7 ± 0.5 Kg. Fruit to plant ratio is 0.6. III. Crown characteristics. The crown is long conical, with weight ranging from 150 to 350 g and 13.1 ± 1.5 cm in diameter. The leaf color is dark green (5 GY 4/6, 4/8) with red mottling (10 R 3/2, 3/4) and in the lower surface is light green (2.5 GY 7/6, 8/6). Leaves have spines usually at the tip and lower part, having an acute apex and acuminate base. The crown has an average amount of 116.2 ± 4.9 leaves. Leaf length and width (cm) vary at the lower (3.8 ± 0.1; 2.3 ± 0.1), middle (11.2 ± 0.6; 2.7 ± 0.2) and upper part (24.3 ± 1.6; 3.4 ± 0.3) of the crown. IV. Flesh and juice characteristics (grade 3). The flesh density is loose to medium, with medium firmness, and medium to strong aroma. Core diameter is 3.0 ± 0.3 cm. Fruit flesh color is an even ivory white. Pulp Brix is stable throughout the year (18.3 ± 0.5), whereas the acidity (0.60 ± 0.0) is seasonal. Table 1 compares fruit quality values for 'HND-32' and its progenitors.

TABLE 1

Comparison of internal fruit quality characteristics at maturity grade 3, between 'HND-32' and parental varieties, under the North Coast of Honduras conditions during July of 2023*.

| Pineapple Variety | Brix (%) | Acid % (g/100 ml Citric acid) | Carotenoids (ppm) | Ascorbic Acid (mg/ml) |
|---|---|---|---|---|
| HND-32* | 18.3 ± 0.5 | 0.60 ± 0.0 | 1.08 ± 0.2 | 0.42 ± 0.0 |
| Dole-11* | 15.8 ± 1.4 | 0.28 ± 0.1 | 12.5 ± 1.8 | 0.43 ± 0.1 |
| Dole-12** | 16.6 ± 1.4 | 1.00 ± 0.2 | 1.03 ± 0.1 | 0.27 ± 0.1 |

*Summer 2023;
**Oct-Nov 2022.

V. Peduncle.—Fruit develops from the apical meristem of the plant on a peduncle, usually 35.0 ±. 1.6 cm in length, and 1.9 ± 0.1 cm in diameter. The peduncle has a waxy texture due to the presence of trichomes and it has a green to light green color at the middle section (5 GY 6/6, 6/8, 6/10).

VI.—Table 2 compares the tolerance of 'HND-32' and known varieties to certain pests, diseases, and other disorders.

TABLE 2

Tolerance comparisons of 'HND-32' and known varieties to certain pests, diseases, and other disorders when grown under the North Coast of Honduras conditions.

| Condition | HND-32 | Dole-12* | Dole-11* | P-1972* |
|---|---|---|---|---|
| *Phytophtora* | high | high | high | moderate |
| *Erwinia* | high | high | high | moderate |
| Army worm | none | none | none | low |
| Mealybug (*pseudococcus brevipes* ) | none | none | none | low |
| Natural Flowering | high | high | low | high |
| Translucency | moderate | low | high | moderate |
| Fruitlet Core Rot | high | high | high | high |
| Internal Brown Spot | high | high | high | high |
| Shell cracking | high | high | high | moderate |
| Open eye | high | high | high | moderate |
| Crown defects | moderate | moderate | moderate | high |

| Condition | Dole-14* | Champaka* | Dole-34* |
|---|---|---|---|
| *Phytophtora* | moderate | high | moderate |
| *Erwinia* | moderate | high | moderate |
| Army worm | low | low | none |
| Mealybug (*pseudococcus brevipes* ) | low | low | none |
| Natural Flowering | high | moderate | moderate |
| Translucency | high | high | high |
| Fruitlet Core Rot | high | moderate | high |
| Internal Brown Spot | high | low | high |
| Shell cracking | high | high | high |
| Open eye | high | high | high |
| Crown defects | high | low | high |

*Dole-12: unpatented; Dole-11: unpatented; P-1972: U.S. Plant Pat. 16,396 P3; Dole-14: U.S. Plant Pat. 20,885 P3; Champaka: unpatented; Dole-34 U.S. Plant Pat. 34,973 P2.

MOLECULAR (DNA) MARKERS FOR 'HND-32'.

Four indel DNA markers were developed using a combination of primers (Table 3) for characterizing 'HND-32'. 'Dole-11' and other known varieties.

TABLE 3

Primers used for generating DNA markers for discriminating between 'HND-32' and other known varieties.

| Primer Name | Primer Sequence (SEQ ID NO:) |
|---|---|
| P1_Forward | AACTGGTATTTGTATTAGCTAAAAAGG (1) |
| P1_Reverse | ATAAACTCCCATGCGTACACT (2) |
| P2_Forward | GATAATCGAAAAGATGTCACTTTACG (3) |
| P2_Reverse | AGTTAATTGTGGATAAGTGGTGG (4) |
| P3_Forward | ATGTGACAAGCGAAGTCAAGC (5) |
| P3_Reverse | ATGCATAATGTGTTCAGTGTTGCT (6) |
| P4_Forward | GGAAAACCAGACACTCCTT (7) |
| P4_Reverse | GATCTGGGCCAACATATGCT (8) |

The PCR program for generating the banding patterns was as follows: First denaturing cycle at 98° C. for 50 seconds, forty cycles of denaturing at 98° C. for 10 seconds, primer annealing at 56° C. for 15 seconds, and extension at 72° C. for 12 seconds, a final extension at 72° C. for 3 minutes, and finally hold at 4° C. PCR products were analyzed by 3% agarose gel electrophoresis. The assignment of genotype A, B and H was as follows:

A: Single, longer PCR product (230 bp-250 bp)

B: Single, shorter PCR product (200 bp-230 bp)

H: Multiple PCR products between 200 bp to 300 bp in size

Figure 5:
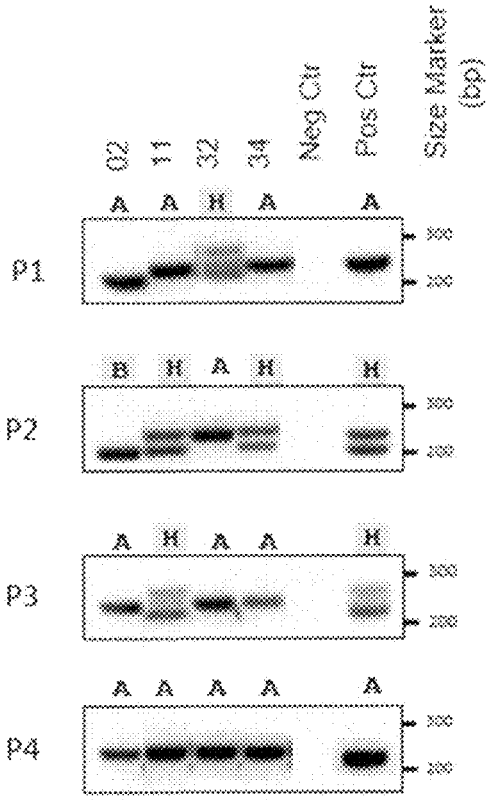
FIG. 5 shows PCR products identified in DNA obtained from pineapples 02 ('P-1972', U.S. Plant Pat. No. 16,396), 11 ('Dole-11', unpatented), 32 ('HND-32', unpatented), 34 ('Dole-34', U.S. Plant Pat. No. 34,973), and Pos Crt ('Dole-11' from grocery, unpatented).

As shown in FIG. 5, the following unique pattern code combining PCR products was identified:

02 ('P-1972'): ABAA 11 ('Dole-11'): AHHA 32 ('HND-32') HAAA 34 ('Dole-34'): AHAA Positive control from grocery ('Dole-11'): AHHA

SEQUENCE LISTING

```
Sequence total quantity: 8
SEQ ID NO: 1            moltype = DNA  length = 27
FEATURE                 Location/Qualifiers
source                  1..27
                        mol_type = other DNA
                        organism = synthetic construct
SEQUENCE: 1
aactggtatt tgtattagct aaaaagg                                    27

SEQ ID NO: 2            moltype = DNA  length = 21
FEATURE                 Location/Qualifiers
source                  1..21
                        mol_type = other DNA
                        organism = synthetic construct
SEQUENCE: 2
ataaactccc atgcgtacac t                                          21

SEQ ID NO: 3            moltype = DNA  length = 26
FEATURE                 Location/Qualifiers
source                  1..26
                        mol_type = other DNA
                        organism = synthetic construct
SEQUENCE: 3
gataatcgaa aagatgtcac tttacg                                     26

SEQ ID NO: 4            moltype = DNA  length = 23
FEATURE                 Location/Qualifiers
```

-continued

```
source                  1..23
                        mol_type = other DNA
                        organism = synthetic construct
SEQUENCE: 4
agttaattgt ggataagtgg tgg                                          23

SEQ ID NO: 5            moltype = DNA  length = 21
FEATURE                 Location/Qualifiers
source                  1..21
                        mol_type = other DNA
                        organism = synthetic construct
SEQUENCE: 5
atgtgacaag cgaagtcaag c                                            21

SEQ ID NO: 6            moltype = DNA  length = 24
FEATURE                 Location/Qualifiers
source                  1..24
                        mol_type = other DNA
                        organism = synthetic construct
SEQUENCE: 6
atgcataatg tgttcagtgt tgct                                         24

SEQ ID NO: 7            moltype = DNA  length = 19
FEATURE                 Location/Qualifiers
source                  1..19
                        mol_type = other DNA
                        organism = synthetic construct
SEQUENCE: 7
ggaaaaccag acactcctt                                               19

SEQ ID NO: 8            moltype = DNA  length = 20
FEATURE                 Location/Qualifiers
source                  1..20
                        mol_type = other DNA
                        organism = synthetic construct
SEQUENCE: 8
gatctgggcc aacatatgct                                              20
```

We claim:

1. A new and distinct variety of pineapple plant designated 'HND-32' substantially, as shown and described herein.

* * * * *